United States Patent [19]

Cianfriglia

[11] Patent Number: 5,766,946

[45] Date of Patent: Jun. 16, 1998

[54] MONOCLONAL ANTIBODIES TO GLYCOPROTEIN P

[75] Inventor: Maurizio Cianfriglia, Rome, Italy

[73] Assignee: Instituto Superiore Di. Sanita', Rome, Italy

[21] Appl. No.: 356,272

[22] PCT Filed: Jun. 16, 1993

[86] PCT No.: PCT/EP93/01533

§ 371 Date: Dec. 15, 1994

§ 102(e) Date: Dec. 15, 1994

[87] PCT Pub. No.: WO93/25700

PCT Pub. Date: Dec. 23, 1993

[30] Foreign Application Priority Data

Jun. 17, 1992 [IT] Italy ................... RM92A0457

[51] Int. Cl.[6] ............... C12N 5/12; C07K 16/28; G01N 33/53

[52] U.S. Cl. ............ 435/331; 435/332; 435/172.2; 435/7.21; 530/388.2; 530/388.85; 530/391.3

[58] Field of Search ............ 424/156.1; 435/7.23, 435/172.2, 240.27, 331, 332, 7.21; 436/548; 530/388.85, 391.1, 388.2, 391.3

[56] References Cited

U.S. PATENT DOCUMENTS 5,206,352   4/1993   Roninson .
5,369,009   11/1994  Arceci .
5,434,075   7/1995   Mechetner .

FOREIGN PATENT DOCUMENTS 0569141   10/1993   European Pat. Off. .
9319094    9/1993   WIPO .

OTHER PUBLICATIONS

Cianfroglia et al. Proceedings Am. Assoc. Canar Res. v. 34:317 Abstract #1889, Mar. 1993.

Chevallier et al. J. Cell Pharmacol 2:165–170, 1991.

Cenciarell;. Int.J. Cancer 47:533–547, 1991.

Hamada et al. NAR 18:1900, 1990.

Bruggemann. Biotechniques 10:202–209 1991.

Seaver, Gen. Eng. News, v.14 No. 114 pp. 10–21, Aug. 1994.

*Primary Examiner*—Lila Feisee
*Assistant Examiner*—Nancy A. Johnson
*Attorney, Agent, or Firm*—Gabriel Lopez; John L. Chiatalas

[57] ABSTRACT

A monoclonal antibody that recognises a structurally continuous and extracellularly-located epitope of human P-glycoprotein is described. The monoclonal antibody has a continuous amino acid sequence, and a binding affinity for the P-glycoprotein which manifests in the ability to stain greater than 90% of live CEM-VBL10 cells in a flow cytometry assay.

11 Claims, 1 Drawing Sheet

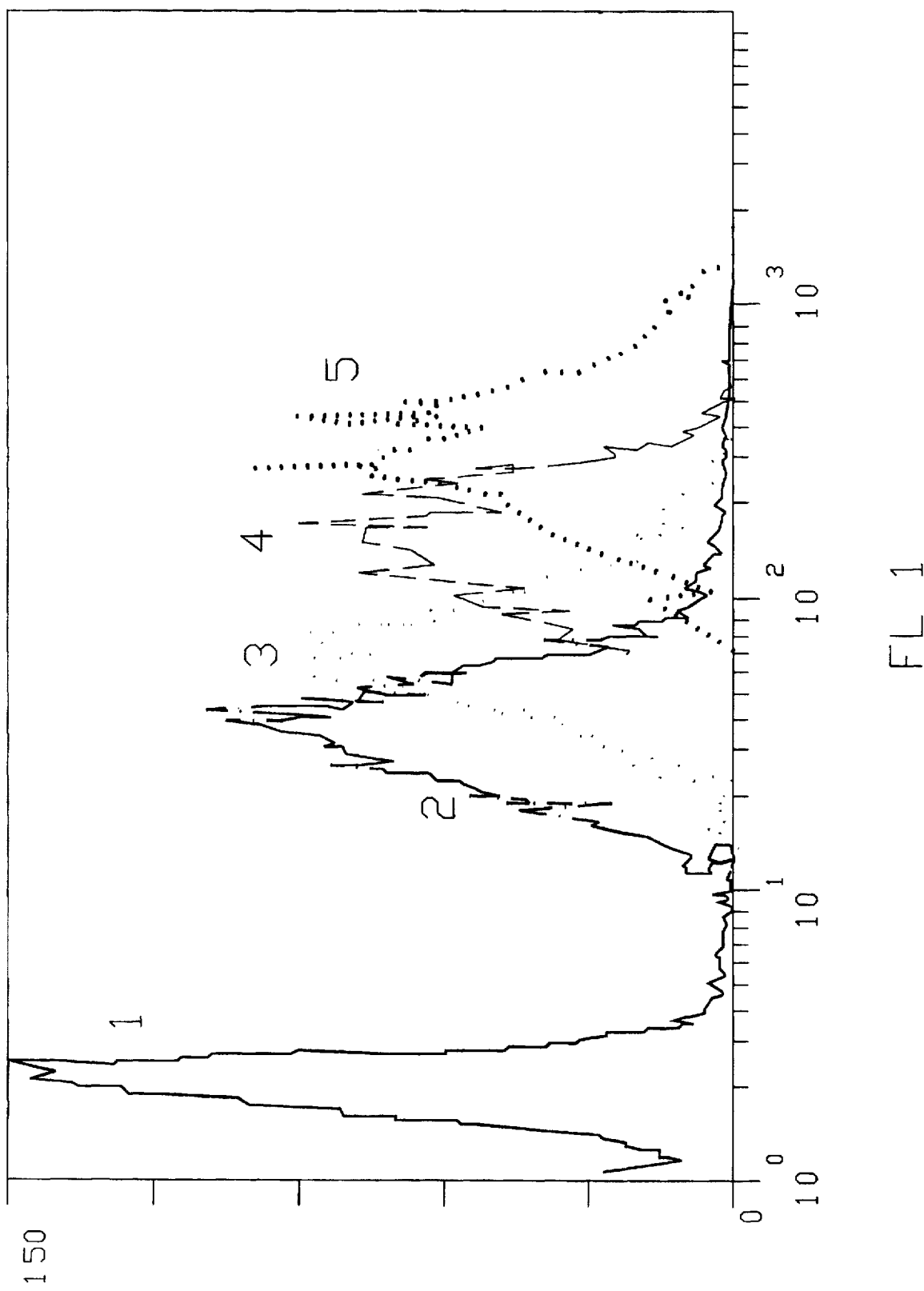

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Homo sapiens ( x i ) SEQUENCE DESCRIPTION: SEQ ID NO: 1:

```
Phe  Thr  Arg  Ile  Asp  Asp  Pro  Glu  Thr  Lys  Arg  Gln  Asn  Ser  Asn  Leu
 1              5                        10                       15
```

( 2 ) INFORMATION FOR SEQ ID NO: 2:

( i ) SEQUENCE CHARACTERISTICS:
        ( A ) LENGTH: 369 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v ) FRAGMENT TYPE: internal ( v i ) ORIGINAL SOURCE:
        ( A ) ORGANISM: Mus musculus
        ( B ) STRAIN: BALB/c ( i x ) FEATURE:
        ( A ) NAME/KEY: CDS
        ( B ) LOCATION: 1..369

( x i ) SEQUENCE DESCRIPTION: SEQ ID NO: 2:

```
CAG  GTC  CAA  CTG  CAG  GAG  TCT  GGA  GGA  GAC  TTA  GTG  AAG  GAT  CCT  GGA    48
Gln  Val  Gln  Leu  Gln  Glu  Ser  Gly  Gly  Asp  Leu  Val  Lys  Asp  Pro  Gly
 1              5                        10                       15

GGG  TCC  CTG  AAA  CTC  TCC  TGT  GCA  GCC  TCT  GGA  TTC  ACT  TTC  AGT  AGA    96
Gly  Ser  Leu  Lys  Leu  Ser  Cys  Ala  Ala  Ser  Gly  Phe  Thr  Phe  Ser  Arg
                20                       25                       30

TAT  GGC  ATG  TCT  TGG  GTT  CGC  CAG  ACT  CCA  GAC  AAG  AGG  CTG  GAG  TGG   144
Tyr  Gly  Met  Ser  Trp  Val  Arg  Gln  Thr  Pro  Asp  Lys  Arg  Leu  Glu  Trp
           35                       40                       45

GTC  GCA  ACC  ATT  AGT  AGC  GGT  GGT  AGT  TAC  ACC  TAC  TTT  CCA  GAC  AGT   192
Val  Ala  Thr  Ile  Ser  Ser  Gly  Gly  Ser  Tyr  Thr  Tyr  Phe  Pro  Asp  Ser
      50                       55                       60

GTG  AAG  GGG  CGA  TTC  ACC  ATC  TCC  AGA  GAC  AAT  GCC  AAG  AAC  ACC  CTG   240
Val  Lys  Gly  Arg  Phe  Thr  Ile  Ser  Arg  Asp  Asn  Ala  Lys  Asn  Thr  Leu
 65                       70                       75                       80

TAC  CTG  CAA  GTG  AGC  AGT  CTG  AAG  TCT  GAG  GAC  ACA  GCC  ATG  TAT  TAC   288
Tyr  Leu  Gln  Val  Ser  Ser  Leu  Lys  Ser  Glu  Asp  Thr  Ala  Met  Tyr  Tyr
                85                       90                       95
```

```
TGT GCA AGA CCT GCG GAA TTT AGG GGT TAC TCC TGG TTT GCT TAC TGG        336
Cys Ala Arg Pro Ala Glu Phe Arg Gly Tyr Ser Trp Phe Ala Tyr Trp
            100                 105                 110

GGC CAA GGG ACC ACG GTC ACC GTC TCC TCA GGT                            369
Gly Gln Gly Thr Thr Val Thr Val Ser Ser Gly
        115                 120
```

( 2 ) INFORMATION FOR SEQ ID NO: 3:

( i ) SEQUENCE CHARACTERISTICS:
        ( A ) LENGTH: 123 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 3:

```
Gln Val Gln Leu Gln Glu Ser Gly Gly Asp Leu Val Lys Asp Pro Gly
 1           5                  10                  15

Gly Ser Leu Lys Leu Ser Cys Ala Ala Ser Gly Phe Thr Phe Ser Arg
            20              25                  30

Tyr Gly Met Ser Trp Val Arg Gln Thr Pro Asp Lys Arg Leu Glu Trp
        35                  40                  45

Val Ala Thr Ile Ser Ser Gly Gly Ser Tyr Thr Tyr Phe Pro Asp Ser
    50              55                  60

Val Lys Gly Arg Phe Thr Ile Ser Arg Asp Asn Ala Lys Asn Thr Leu
 65             70                  75                      80

Tyr Leu Gln Val Ser Ser Leu Lys Ser Glu Asp Thr Ala Met Tyr Tyr
            85                  90                      95

Cys Ala Arg Pro Ala Glu Phe Arg Gly Tyr Ser Trp Phe Ala Tyr Trp
            100                 105                 110

Gly Gln Gly Thr Thr Val Thr Val Ser Ser Gly
        115                 120
```

( 2 ) INFORMATION FOR SEQ ID NO: 4:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Homo sapiens ( x i ) SEQUENCE DESCRIPTION: SEQ ID NO: 4:

```
Gly Pro Gly Asp Asp Ala Val Lys
 1           5
```

MONOCLONAL ANTIBODIES TO GLYCOPROTEIN P

The present invention relates to monoclonal antibodies which have specificity for P-glycoprotein (Pgp). More particularly, the invention relates to monoclonal antibodies to an extracellular epitope of human Pgp and to their preparation and diagnostic and clinical uses.

The present description refers to various publications by reference numbers in brackets and these are listed towards the end of the text.

The development by Kohler and Milstein (1) of somatic cell fusion techniques for the production of hybrid cell lines which produce monoclonal antibodies has made it possible to prepare unlimited quantities of homogeneous antibody products which have-defined specificity for single antigenic determinants. The portion of a protein antigenic determinant that is recognised by and reacts with an antibody is known, and referred to herein, as the epitope and consists of one or more specific epitope-forming amino acid sequences.

Glycoprotein P is a plasma membrane protein which is over-expressed on the surfaces of cell lines or human tumour cells that exhibit an intrinsic or acquired multidrug-resistant (MDR) phenotype. The expression of this protein gives the cells the ability to multiply actively in the presence of concentrations of cytostatic drugs that are toxic for non-MDR parent cells. Transfection studies using cloned Pgp cDNAs have demonstrated the direct role of this protein in mediating the MDR phenotype (2). Pgp is thought to function as an energy-dependent drug efflux pump.

The amino acid sequence of Pgp has been deduced from the nucleotide sequences of the genes that confer the MDR phenotype in recipient cells (2, 3, 4). The secondary structure of Pgp has been predicted from analysis of its primary structure and is that of a transmembranal protein consisting of 12 hydrophobic transmembranal helices linked via 6 hydrophilic extracellular loops and 2 large cytoplasmic domains encoding 2 ATP-binding sequences.

A number of different monoclonal antibodies to Pgp have been isolated and characterised, and the specificities of some of these are reviewed by Cenciarelli et al. (5). More recently further monoclonals have been described which have specificity for the extracellular domain of Pgp (6, 7, 8). However monoclonal antibodies to Pgp for which the specific epitope-forming amino acid sequences have been characterised react either with the cytoplasmic domain of Pgp or with extracellular epitopes comprising discontinuous portions of the amino acid sequence of the protein. For example, Georges et al. (8) have mapped the epitope of the monoclonal antibody MRK-16, described by Hamada and Tsuruo (9), which comprises peptides present on 2 of the 6 extracellular peptide loops (the 1$^{st}$ and the 4$^{th}$), predictable from the primary amino acid sequence.

Monoclonal antibodies to Pgp have been proposed for diagnostic and clinical uses, e.g. to monitor the level of Pgp expression on, and thereby the multi drug resistance (mdr) status of, human cells. Also such antibodies may find uses in the inhibition of Pgp-mediated MDR (7).

None of the known monoclonal antibodies to Pgp recognises a human-specific, extracellular epitope of glycoprotein P consisting of a continuous epitope-forming amino acid sequence. Moreover there is a continuing need for antibodies which are capable of recognising low levels of Pgp; for instance, when expressed on MDR cells at low levels or when the MDR cells are present as only a low proportion of a cell population. Monoclonal antibodies capable of recognising such human-specific epitopes and low Pgp levels would be useful for immunological testing.

Using the above mentioned somatic cell fusion techniques, a hybridoma secreting a monoclonal antibody (MM4.17) has been obtained which is capable of selective, high affinity binding to a previously unknown continuous extracellular epitope of human Pgp.

FIG. 1 is a graph showing FACS analysis results for human Pgp expression, according to the invention.

Accordingly the present invention provides a monoclonal antibody that recognises a structurally continuous and extracellularly-located epitope of human Pgp consisting of a continuous epitope-forming amino acid sequence.

For the purposes of the present description "human Pgp" refers to the product of the human MDR1 gene. Also the term "monoclonal antibody" encompasses whole antibody molecules and antigen binding fragments thereof, including FAb, F(Ab')$_2$, Fv fragments and single domain antibodies, and is not limited to products derived from hybridoma cell lines but also includes antibody molecules and antigen-binding fragments thereof when produced by recombinant DNA techniques, i.e. expressed from cloned antibody coding DNA sequences.

The epitope-forming amino acid sequence which is recognised by the antibody may be located on any one of the extracellular loops of human Pgp. Preferably the epitope-forming amino acid sequence is located on the fourth loop of human Pgp. More preferably the epitope is contained in the human Pgp peptide having the sequence: FTRIDDPET-KRQNSNL (SEQUENCE ID NO.1 of the accompanying SEQUENCE LISTING). Even more preferably, the epitope comprises at least 5 contiguous amino acid residues of the 8 amino acids of the peptide consisting of residues 2 to 9 inclusive of SEQUENCE ID NO.1 and still more preferably the 5 amino acids are amino acid residues 3 to 7 inclusive of SEQUENCE ID NO.1.

In a particular embodiment of the invention the monoclonal antibody may have a variable domain amino acid sequence comprising Complementarity Determining Regions (CDRs) in which each CDR is the same as or a variant of the corresponding CDR given hereinafter in SEQUENCE ID NOs. 2 and 3 (i.e. the CDRs of the heavy chain variable domain of the monoclonal antibody MM4.17).

In the amino acid sequence given in SEQUENCE ID NOs. 2 and 3 CDR1 corresponds to amino acid residues 32 to 36 inclusive, CDR2 to amino acid residues 51 to 67 inclusive and CDR3 to amino acid residues 100 to 111 inclusive. The remainder of the amino acid sequence given in SEQUENCE ID NOs. 2 and 3 comprises framework regions (FR1, FR2, FR3 and FR4 in N terminal to C terminal direction) which may be changed for other framework regions without substantially effecting the antigen binding characteristics of the variable domain.

For the purposes of the present description a variant of a CDR sequence is a sequence which is at least 70%, preferably at least 80%, more preferably at least 90%, particularly at least 95% homologous to a reference CDR sequence, e.g. CDR1, CDR2 or CDR3 of the amino acid sequence given in SEQUENCE ID NOs. 2 and 3.

Surprisingly, compared with the known monoclonal antibodies, the monoclonal antibody MM4.17 has a very high degree of affinity for MDR cells and is capable of detecting even the minimal levels of acquired multidrug resistance of CEM-VBL10 cells (10, 11). MM4.17 is also capable of detecting the acquired multidrug resistance of CEM-VBL16 cells (11). The relative resistance (RR) of this cell line to vinblastine is 6.25. The CEM-VBL10 and CEM-VBL16 cell lines are MDR derivatives of the drug sensitive CEM cell line (see reference 11, deposited as ATCC CCL 119) obtained by selection in medium containing 10 ng/ml and 16 ng/ml respectively of vinblastine.

Thus in a particularly preferred embodiment the invention includes monoclonal antibodies of the invention which have binding affinities for Pgp similar to that of MM4.17, e.g. monoclonal antibodies capable of detecting the acquired multidrug resistance of CEM-VBL10 or CEM-VBL16 cells or similar MDR cells.

A comparison of the binding affinities of the MM4.17 antibody and previous anti-Pgp monoclonals C219 (15), C494 (15), JSB1 (16), MRK-16 (9) and MC57 (5) for Pgp on drug-sensitive parent CEM and MDR derivative cell lines CEM-VBL10 and CEM-VBL100 is given hereinafter in Example 6. The MDR cell lines CEM-VBL10, CEM-VBL16 and CEM-VBL100 are described by and obtainable from Beck et al. (11). Similar MDR cell lines may be obtained substantially as described by Beck et al.

Monoclonal antibodies according to the invention may be prepared using standard techniques. Thus hybridoma cell lines may be prepared by somatic cell fusion techniques using spleen cells obtained from animals which have been immunised with human MDR cells. Any suitable human MDR cell line may be used including MDR cell lines derived from drug sensitive parent cell lines, such as the MDR cell line CEM-VBL100 described by Beck et al. (11) or similar MDR cell lines. CEM-VBL100 is an MDR derivative of the drug sensitive CEM cell line which is deposited with the American type culture Collection as ATCC CC1 119.

More conveniently peptides corresponding to extracellular domains of human Pgp or fragments thereof may be used for immunisation. Any suitable human Pgp extracellular domain peptide may be used. For example, peptides corresponding to the fourth loop of Pgp or fragments thereof, such as the peptide of SEQUENCE ID NO.1 or the fragments thereof discussed above may be used as antigens.

Preferably immunisation procedures which favour the generation of high affinity monoclonals are used, such as the procedures described by Cianfriglia et al. (12), and similar procedures.

Hybridomas which produce the desired monoclonal antibodies may be identified by their ability to bind preferentially to human MDR cells as compared to drug-sensitive cells, followed by selection for those which are specific for structurally continuous extracellularly-located epitopes. Preferably peptides corresponding to structurally continuous extracellular domains of human Pgp or parts thereof, such as the preferred peptides discussed above, are used to screen for the desired monoclonal antibodies.

Monoclonal antibodies may be prepared from the hybridoma cell lines using cell culture and ascites techniques. Antibody fragments may be prepared using appropriate techniques such as enzymic cleavage. Recombinant products may be produced by processes involving transformation or transfection of suitable host cells with DNA sequences which code for the whole molecule or fragment monoclonal products and culturing of the transformed host cells to produce the products.

The antibody can be used advantageously: to detect the presence of Pgp in normal and tumour tissues with the aid of immunofluorescent or immunochemical methods; in in-vitro tests to identify cells with the MDR phenotype; for methods of enriching specific cell populations in which Pgp is present (stem cells, cells infected with HIV, T lymphocytes).

Thus the invention also includes suitably labelled, e.g. fluorescently labelled monoclonal antibodies according to the invention, as well as products in forms suitable for immunopurification or immunoenrichment, e.g. in which the monoclonal antibody is immobilised on a suitable solid phase such as polymer particles.

Hybridomas and other cell lines, including transformed host cell lines, which produce monoclonal antibodies according to the invention are also included in the invention.

Immunological diagnostic kits containing as specific reagent a monoclonal antibody according to the invention for the detection of MDR cells or human Pgp are also included in the invention. Such kits typically comprise a suitably labelled monoclonal antibody according to the invention, e.g. a fluorescently labelled antibody.

The invention also includes the use of a monoclonal antibody according to the invention for the identification or purification of cells expressing human Pgp present in heterogeneous cell populations.

Moreover the invention also includes use of a monoclonal antibody of the invention as a therapeutic agent, e.g. to reverse MDR, and also to therapeutic compositions comprising the monoclonal antibodies. The monoclonals may be used in any of those situations in which MDR presents a clinical problem, including cancer treatment. The therapeutic compositions typically comprise an antibody according to the invention in combination with a pharmaceutically acceptable carrier or excipient.

The present invention is now described by way of illustration only in the following Examples which refer to the accompanying. FIG. 1 which is a graph showing FACS analysis results for human Pgp expression on live CEM cells and its MDR variants as determined using monoclonal antibody MM4.17 (1=drug-sensitive CEM line; 2=CEM-VRL20; 3=CEM-VRL40; 4=CEM-VRL80; 5=CEM-VRL100. Abscissae: fluorescence intensity; ordinates: number of cells).

EXAMPLES

Example 1

Immunization of mice and hybridization of splenocytes with cells of the myeloma line SP2-01/Ag.14 (ATCC CRL 1581)

BALB/c mice are immunized with an MDR variant of a human T-lymphoblastoid line already characterized and known as CEM-VBL100 (11). The derivation of the CEM-VBL100 cell line from the parent CEM cell line (ATCC CCL 119) is described by Beck et al. (11) from whom this cell line and other MDR derivatives of CEM are available. The cells of the CEM-VBL100 line proliferate actively in the presence of 100 ng/ml vinblastine or relatively high concentrations of a wide range of cytostatic agents. In order to obtain high affinity monoclonals, immunisation procedures substantially as described by Cianfriglia et al. (12) are used, with appropriate modifications. The immunization procedure involves the intraperitoneal administration of $1 \times 10^7$ CEM-VBL100 cells resuspended in PBS, live and with no pretreatment, every 15 days for 10 months. The last immunization takes place 3 days before the somatic fusion of splenocytes taken from the treated mice and involves the administration of $2 \times 10^7$ cells (resuspended in PBS) into the caudal vein and of the same number of cells intraperitoneally.

After thorough washing with serum-free culture medium, $25 \times 10^6$ splenocytes are placed in a test tube with $10-10^6$ Sp2-01/Ag.14 myeloma cells (ATCC CRL 1581), pretreated in the same way as the lymphocytes.

The mixture of spleen cells and myeloma cells is then processed as described by Cianfriglia et al. (12). Briefly, the heterokaryons obtained are distributed on microtitration plates (Costar) to obtain, after selection in HAT culture medium (H=hypoxanthine, A=aminopterin, T=thymidine, Gibco), clonal hybridomas. The culture supernatants from the cells in which increased cell growth is observed are tested for indirect immunofluorescence with the CEM drug-sensitive parent line (ATCC CCL 119) and, simultaneously, with the CEM-VBL100 variant, to identify hybridomas secreting immunoglobulins that react selectively to the MDR immunizing cell and do not cross-react with the drug-sensitive parent line. From the hybridoma lines thus selected a line is identified, known as MM4.17, that secretes immunoglobulins of isotype IgG2a,k, which are highly reactive to the CEM-VBL100 cells, as demonstrated by an intense immunofluorescence signal, determined by flow cytofluorimetry studies, shown in FIG. 1. Flow cytometry determinations are performed using standard procedures with FITC-conjugated F(Ab')$_2$ anti-mouse IgG (Cappel, West Chester, Pa., USA). After staining cells were fixed with 1% formaldehyde in PBS, pH7.2 and analysed on a bench-top flow cytometer (FACScan, Becton Dickinson) equipped with a 15-nW argon ion laser emitting light at a fixed wavelength of 488 nm.

The MM4.17 hybridoma is seeded onto 96-cell microtitration plates at a concentration of 0.5 cells per cell on a single layer of cells to provide nutrients (feeder layer) obtained by peritoneal lavage of BALB/c mice. Culture medium containing HT (100 μL) is added to each cell and, after 10–14 days culture, the clones are sub-cloned by the same procedure as described above a further two times. The sub-clones secrete an antibody with the same characteristics as that produced by the non-cloned line.

The MM4.17 hybridoma is cultured in vitro to obtain large quantities of monoclonal antibody from the supernatant and is injected into syngeneic BALB/c mice that have been pre-treated with Freund's incomplete adjuvant to promote the formation of ascites.

Any similar MDR human cell line may be used in place of the CEM-VBL100 for immunisation of the mice and selection of hybridoma cell lines.

Example 2

Specificity of the MM4.17 monoclonal antibody for human MDR1- P-glycoprotein The supernatant of the hybridoma cell line MM166.4.17 (now known as MM4.17) binds only with the human MDR variants of CEM cells (as described in references 10 and 11) and is completely unreactive with its drug-sensitive parental cell line. After two cloning cycles, a cloned hybridoma cell line secreting an IgG2a, k, monoclonal immunoglobulin is isolated, characterised, and a hybridoma cell bank is set up from large-scale mycoplasma-free cultures. From this cell bank, vial samples are thawed and hybridoma cells tested for stability, sterility and specificity. Additional working cell banks are made and consistent and homogeneous batches of monoclonal antibody in either purified or crude form are obtained from the supernatants thereof. FIG. 1 shows the fluorescence profiles of the monoclonal MM4.17 on CEM cells and MDR variants thereof possessing various levels of relative resistance (RR). These data clearly show the capability of MM4.17 to recognise very low RR levels (see references 10 and 13) and variations of P-glycoprotein expression on MDR cells. The MM4.17 monoclonal strongly stains only the MDR variants of the various human cell lines tested and does not significantly stain either drug-sensitive or drug-resistant cells of rodent origin. The specificity of the MM4.17 antibody is also confirmed by somatic cell genetics studies. Interspecific hybrids obtained by somatic fusion of a rodent drug-sensitive cell line with the CEM-VBL100 cells segregate according to MDR phenotype, the MDR1 gene and antigenic determinant being recognised by the MM4.17 antibody.

Example 3

Identification of the epitope of glycoprotein P recognised by the MM4.17 antibody Peptides are synthesized that have the amino acid sequences deduced from the portions of the cDNAs that code for the extracellularly-located domains of human or murine glycoprotein P (2, 3, 4). These peptides are incubated with the culture supernatant of the hybridoma secreting the MM4.17 antibody. An ELISA assay is used to show that the peptide corresponding to residues 739–754 of the fourth extracellular loop of Pgp (SEQUENCE ID NO. 1) is capable of reacting with the MM4.17 antibody. The other peptides from the predicted extracellular P-glycoprotein domains do not interact with antibody. Also no detectable binding is seen with mouse peptides which correspond to equivalent parts of the predicted mouse mrdl extracellular domains. For example, MM4.17 does not cross-react with peptides representing stretches of the fourth extracellular loop of the mouse mdr1-P-glycoprotein, in spite of the relatively high degree of homology between the human and mouse peptide sequences.

To define the minimum sequence capable of reaction with the MM4.17 antibody an overlapping series of 70 tetra to-decapeptides, contained in SEQUENCE. ID NO. 1, are synthesized and subjected to an ELISA assay with the MM4.17 antibody. The series consists of 10 sets of tetra to decapeptides, the first set having a tetrapeptide corresponding to amino acid residues 1 to 4 and a decapeptide corresponding to amino acid residues 1 to 10 of SEQUENCE ID NO. 1 and the second set having a tetrapeptide corresponding to amino acid residues 2 to 5 and a decapeptide corresponding to amino acid residues 2 to 11 of SEQUENCE ID NO. 1 and so on for each successive set tetra to decapeptides. The ELISA assay results indicate that the octapeptide consisting of residues 2 to 9 inclusive of SEQUENCE ID NO.1 is the optimum minimum epitope. The loss of the first, and even more so that of the last, threonine produces a marked loss of the capacity to bind the MM4.17 antibody. Analysis of antibody binding to the various peptides clearly shows that: (1) binding is significantly reduced if the optimum minimum sequence is elongated in either direction; (2) the hexapeptide consisting of residues 4 to 9 inclusive of SEQUENCE ID NO.1 represents the core of the antibody recognition site, since it is found in all of the positive peptides; and (3) the specificity of the MM4.17 antibody is underlined by very significant binding values obtained with shorter peptides, such as those consisting of residues 3 to 8, 4 to 9 and 4 to 8 inclusive of SEQUENCE ID NO.1.

Example 4

Specificity of MM4.17 for the human MDR1 gene product

The mdr specificity of the MM4.17 monoclonal is determined by assaying its binding to octapeptides of the predicted amino acid sequences of other mammalian P-glycoprotein genes which are selected for their homology to the specific epitope-forming amino acid sequence of the optimal-minimal peptide. The MM4.17 monoclonal does not bind either to the corresponding peptide (SEQUENCE ID NO. 4) of the highly divergent second member of the human mdr gene family MDR3 (identical sequences are found in mouse mdr2 and hamster pgp3 glycoproteins) or to mouse mdr1, mdr3 and hamster pgp1 and pgp2 P-glycoprotein peptides which are most similar to the MDR1 optimum minimum epitope-forming peptide.

Example 5

Identification of the nucleotide sequence and amino acid sequence of the variable region of the heavy chain of the antibody MM4.17

The cDNA sequence coding for the variable domain and hypervariable portions thereof of the heavy chain of MM4.17 is obtained as described by Orlandi et al. (14). The cDNA and corresponding predicted amino acid sequences are given below in SEQUENCE ID NO. 2 and the amino acid sequence alone is given as SEQUENCE ID NO. 3. The Complementarity Determining Regions (CDRs) are residues 32 to 36 inclusive (for CDR1), residues 51 to 67 (for CDR2) and residues 100 to 111 (for CDR3) of the heavy chain variable domain amino acid sequence given in SEQUENCE ID NOs 2 and 3.

Example 6

Comparison of the binding affinity of MM4.17 for Pgp on MDR and drug-sensitive cells with previous monoclonals The MM4.17 and previous monoclonals C219, C494, JSB1, MRK-16 and MC57 are compared for binding to CEM, CEM-VBL10 and CEM-VBL100 in flow cytometry experiments in which the staining characteristics of fluorescently labelled versions of the antibodies are measured. The results obtained are given in the Table below. The monoclonals were used in purified form and at the same protein concentration (10 μg/ml). The results clearly show that the MM4.17 has substantially higher binding affinity for MDR cell lines and is the monoclonal which unequivocally binds to the CEM-VBL10 cell line.

TABLE

| MAb | Pgp domain | cells | | | CEM/CEM-VBL10 fluorescent profile | CEM-VBL100 fluorescent profile |
| --- | --- | --- | --- | --- | --- | --- |
| | | CEM | CEM-VBL10 | CEM-VBL100 | | |
| C219 | cyt[1] | +−[2] | +− | + | yes[3] | yes |
| C494 | cyt | +− | +− | ++ | yes | yes |
| JSB1 | cyt | +− | +− | + | yes | yes |
| MRK-16 | ext[4] | − | +− | +++ | yes | no |
| MC57 | ext | − | +− | +++ | yes | no |
| MM4.17 | ext | − | +++ | ++++ | no | no |

In the above Table the reference numbers have the following significances:
[1]cytoplasmic epitope recognition (the cells have to be fixed or permeabilised for MAb staining.
[2]level of reactivity: −, negative; +−, from 5 to 30%; +, from >30 to 60%; ++, from >60 to 90%; +++, from >90 to 100%; ++++, 100% of the cells stained but with a higher fluorescent intensity.
[3]the fluorescent profiles of the cells show an overlapping area of reactivity.
[4]extracellular epitope recognition in live human MDR cells.

REFERENCES

1. Kohler G. and Milstein C., Nature, 256, 495, 1975
2. Ueda et al. (1987), PNAS, 84, 3004–3008.
3. Shen et al. (1986), Mol. Cell. Biol., 6, 4039–4044.
4. Chen et al. (1987), Cell., 47, 381–389.
5. Cenciarelli et al.,(1991) Int. J. Cancer, 47, 533–544.
6. Arceci et al. (1993) Cancer Res., 53, 310–317.
7. Mechtner & Roninson (1992) PNAS, 89, 5824–5828.
8. Georges et al. (1993) JBC, 268, 1792–1798.
9. Hamada and Tsuruo (1986), PNAS, 83, 7785–7789.
10. Cianfriglia et al. (1990) Int. J. of Cancer, 45, 95–103.
11. Beck et al. (1979) Cancer Res., 39, 2070–2077.
12. Cianfriglia et al., (1986) Meth. in Enzymol., 121, 193–210.
13. Wyler et al. (1993) Proceedings of the 84th Annual Meeting of AACR, Abs. No. 1837, page 309.
14. Orlandi et al., (1989) PNAS, 86, 3833–3837
15. Kartner et al. (1985), Nature, 316, 820–823.
16. Scheper et al. (1988), Int. J. Cancer, 42, 389–394.

I claim:

1. A monoclonal antibody that recognizes a structurally continuous and extracellularly-located epitope of human P-glycoprotein consisting of a continuous amino acid sequence, and which has a binding affinity for P-glycoprotein such that it is capable of staining greater than 90% of live CEM-VBL10 cells when tested in a flow cytometry experiment.

2. A monoclonal antibody of claim 1 in which the said amino acid sequence is located on the fourth extracellular loop of human P-glycoprotein.

3. A monoclonal antibody of claim 2 in which the said amino acid sequence is contained in the peptide of SEQUENCE ID NO. 1.

4. A monoclonal antibody of claim 3 in which the said amino acid sequence comprises at least 5 contiguous amino acid residues of the 8 amino acid sequence consisting of residues 2 to 9 inclusive of SEQUENCE ID NO. 1.

5. A monoclonal antibody of claim 4 in which the 5 amino acids are residues 3 to 7 inclusive of SEQUENCE ID NO. 1.

6. A monoclonal antibody of claim 1 comprising a variable domain having CDRs, CDR1, CDR2 and CDR3, which have amino acid sequences which are the same as the amino acid sequences of the corresponding CDRs of the heavy chain variable domain of SEQUENCE ID NO. 2.

7. A monoclonal antibody of claim 1 which is fluorescently labeled or immobilised on a solid phase.

8. A method for the preparation of a monoclonal antibody of claim 1, comprising 1) somatic cell fusion of spleen cells obtained from an animal which has been immunised with human multidrug-resistant cells or peptides corresponding to extracellular domains of human P-glycoprotein or fragments thereof; and 2) selection of an antibody with the specificity of said antibody of claim 1.

9. A method of claim 8 in which a peptide corresponding to a structurally continuous extracellular domain of human P-glycoprotein or a part thereof is used to screen for the desired monoclonal antibody.

10. Hybridoma and transformed host cell lines producing a monoclonal antibody according to either of claims 1, 2, 3, 4, 5, 6, or 7.

11. An immunological diagnostic kit containing as specific reagent a monoclonal antibody according to either of claims 1, 2, 3, 4, 5, 6, or 7 for the detection of human multidrug-resistant cells or human P-glycoprotein.

* * * * *